United States Patent [19]

Hsieh

[11] Patent Number: 5,473,663

[45] Date of Patent: Dec. 5, 1995

[54] METHOD FOR EVALUATING THE PERFORMANCE OF DETECTORS IN A COMPUTED TOMOGRAPHY SYSTEM

[75] Inventor: Jiang Hsieh, Waukesha, Wis.

[73] Assignee: General Electric Company, Milwaukee, Wis.

[21] Appl. No.: 303,799

[22] Filed: Sep. 12, 1994

[51] Int. Cl.$^6$ ............................................ G01D 18/00
[52] U.S. Cl. ............................ 378/207; 378/18; 378/19
[58] Field of Search ............................... 378/4, 18, 19, 378/207, 204

[56] References Cited

U.S. PATENT DOCUMENTS

| | | | |
|---|---|---|---|
| 4,352,020 | 9/1982 | Horiba et al. | 378/18 |
| 4,663,772 | 5/1987 | Mattson et al. | 378/18 |
| 4,818,943 | 4/1989 | Chandra | 378/207 X |
| 4,873,707 | 10/1989 | Robertson | 378/207 X |
| 4,991,189 | 2/1991 | Boomgaarden et al. | 378/4 |
| 5,301,108 | 4/1994 | Hsieh | 364/413.19 |

*Primary Examiner*—David P. Porta
*Attorney, Agent, or Firm*—Quarles & Brady

[57] ABSTRACT

An x-ray CT scanner is operated in a test mode to acquire attenuation projections using a phantom shaped to accentuate errors due to non-uniform detector response along the z-axis. Error values are calculated for detector elements and these error values are compared with preset limits to identify faulty or marginal detector elements.

5 Claims, 5 Drawing Sheets

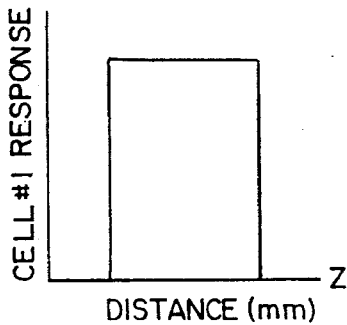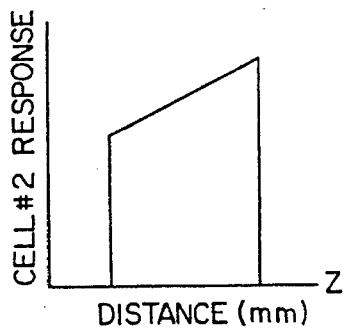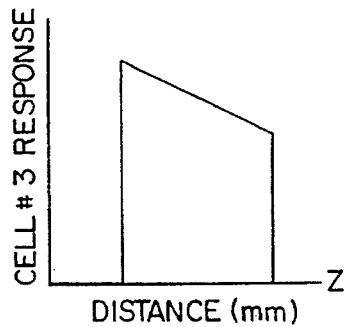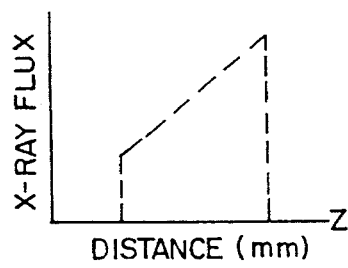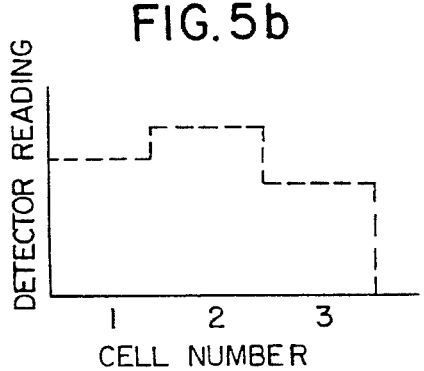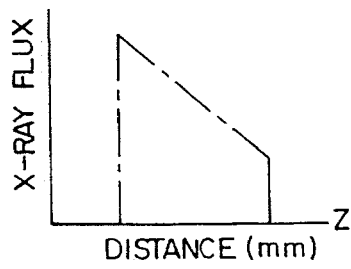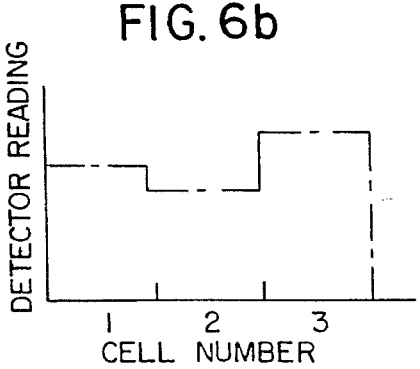

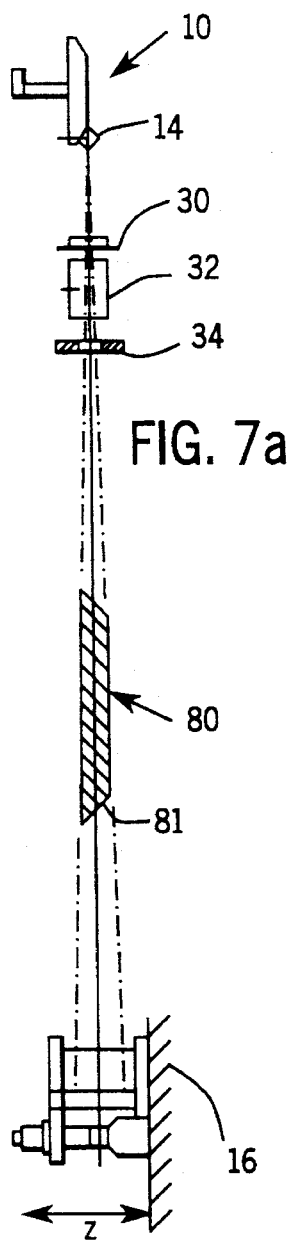
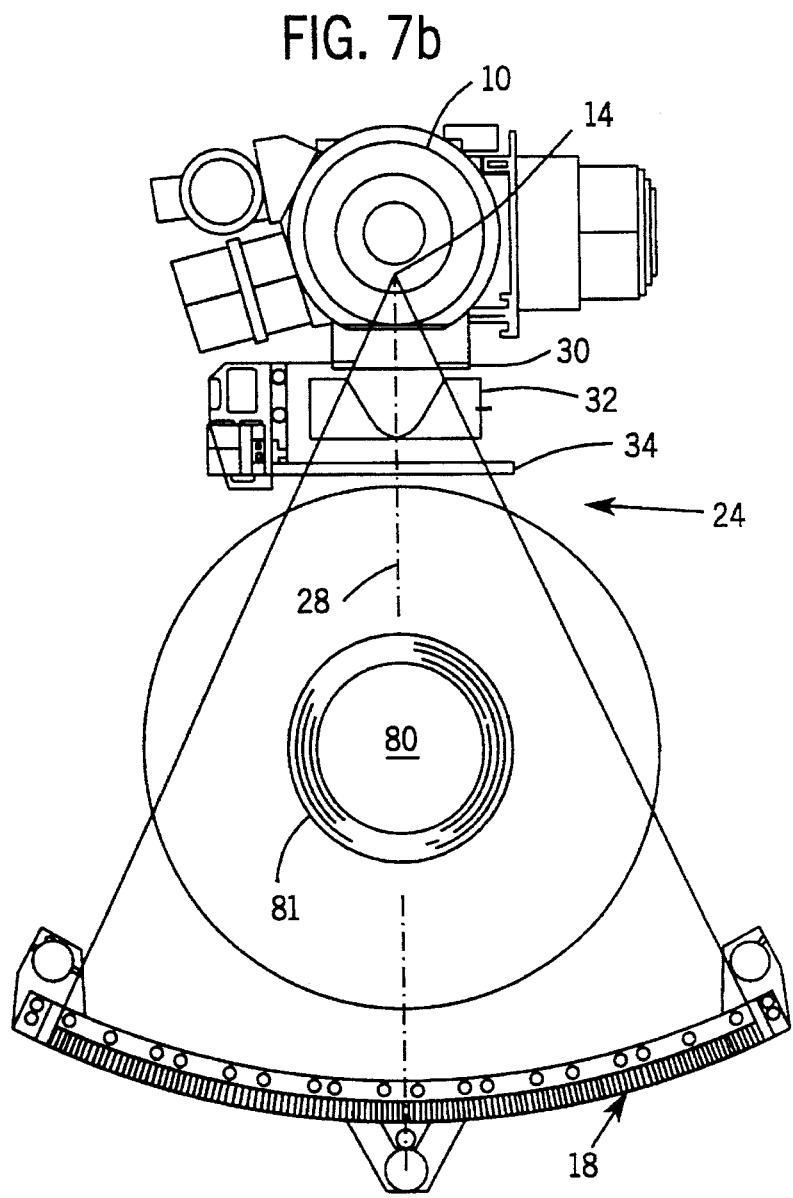

5,473,663

METHOD FOR EVALUATING THE PERFORMANCE OF DETECTORS IN A COMPUTED TOMOGRAPHY SYSTEM

BACKGROUND OF THE INVENTION

This invention relates to computed tomography equipment and specifically to image artifacts caused by variations in x-ray detector sensitivity along the z-axis.

Computed tomography (CT) systems, include an x-ray source collimated to form a fan beam, the fan beam extending generally along a fan beam plane and directed through an object to be imaged. After passing through the imaged object, the fan beam is received by an x-ray detector array extending along the fan beam plane. The x-ray source and detector array are rotated together on a gantry within an imaging plane, generally parallel to the fan beam plane, around the image object.

The axis of rotation of the gantry is designated as the z-axis of the Cartesian coordinate system and the fan beam plane and imaging plane is parallel to the x-y plane of the coordinate system.

The detector array is comprised of detector cells each of which measures the intensity of transmitted radiation along a ray from the x-ray source to that particular detector cell. At each gantry angle, a projection is acquired comprised of intensity signals from each of the detector cells. The gantry is then rotated to a new gantry angle and the process is repeated to collect a number of projections along a number of gantry angles to form a tomographic projection set.

Each tomographic projection set is stored in numerical form for later computer processing to "reconstruct" a cross sectional image according to methods known in the art. The reconstructed image may be displayed on a conventional CRT or may be converted to a film record by means of a computer driven camera.

Ideally, the fan beam plane will strike the center line of the detector array. In practice, however, the fan beam plane may be displaced along the z-axis from the center line because of two effects. The first effect is the thermal expansion of the x-ray tube's anode and its support. The surface temperature of the tube's anode may rise as high as 2,000° C. and the anode supporting structure may rise to 400° C. or more. This heating and the resulting expansion of the tube's anode and its support causes a shifting of the focal spot of the tube which moves the point from which the x-rays emanate. The shifting of the focal spot causes a corresponding shift in the fan beam plane.

The second effect is the mechanical deflection of the gantry and anode support as the gantry rotates. This deforming stress results from the changing angle of gravitational acceleration and the changing magnitude of centripetal acceleration as a function of the rotational velocity of the gantry, acting both on the gantry and anode.

Displacement of the fan beam plane along the z-axis of the detector array is a problem because it causes variations in detector signals that are "exogenous" or unrelated to the internal structure of the imaged object. Generally each detector cell's sensitivity to x-rays will be a function of the x-axis position of the fan beam along the surface of that cell, that is, the detector cells exhibit a non-uniform "z-axis sensitivity". This z-axis sensitivity, combined with motion of the fan beam plane on the detectors, produces the undesired variations in the strength of the detector signal. Such exogenous variations in the detector signals produce undesirable "z-axis artifacts" in the reconstructed image.

Displacement of the fan beam plane and thus variations in the detector signals may be predicted and corrected. In U.S. Pat. No. 4,991,189, issued Feb. 5, 1991, assigned to the same assignee as the present invention, and incorporated by reference, a control system using a movable collimator adjusts the z-axis position of the fan beam plane as deduced from a pair of special detector cells. The special detector cells provide information to a computer model of the system which in turn is used to control the collimator and to correct the placement of the fan beam plane. While such closed loop controls of the fan beam location reduce z-axis artifacts, they do not eliminate the problem.

Intercell sensitivity can be corrected using data from a calibration scan performed before a patient is in place. However, such corrections do not eliminate artifacts due to variations in detector sensitivity along the z-axis. Consider, for example, the z-axis sensitivity profiles of three different detector cells #1–3 in FIGS. 4(a)–4(c). Detector cell #1 represents a perfect sensitivity profile, while detector cells #2 and #3 represent actual sensitivity profiles with different characteristics. If these three detector cells are exposed to an x-ray flux which is uniform, the detector responses will differ because of the different z-axis sensitivities profiles, but these can be corrected using the calibration data.

Consider, however, the situation in which the x-ray flux is not uniform along the z-axis, but is instead variably attenuated by the patient being imaged. One such x-ray flux density profile is shown in FIG. 5(a), and the resulting response of these three detector cells after air calibration are shown in FIG. 5(b). On the other hand, consider a different x-ray flux density profile as shown in FIG. 6(a) and the resulting response of the same three detector cells after air calibration in FIG. 6(b). Methods such as that disclosed in U.S. Pat. No. 5,301,108 entitled "Computed Tomography System With Z-Axis Correction" have been developed to correct z-axis artifacts, and they work until the detector sensitivity profile deteriorates beyond reasonable limits.

To reduce the chance of misdiagnosis due to z-axis artifacts a test is conducted on x-ray detectors in the field to determine their status. Scan data is gathered in the field and sent to the manufacturer for manual analysis. The reconstructed images are inspected and the results are rated by a jury panel to determine the fate of each detector. This process is very costly and time consuming and an automated procedure for periodically evaluating x-ray detector performance is needed.

SUMMARY OF THE INVENTION

The present invention relates to a method for testing the detector elements in an x-ray CT system to identify those which have deteriorated. More specifically, the invented method includes acquiring one or more sets of attenuation signals using a reference phantom that accentuates detector element z-axis errors; calculating an error value for each of a plurality of the detector elements by comparing their attenuation signals with a model curve; and comparing the error values with a preset limit and indicating which detector element error values exceed the preset limit.

A general object of the invention is to identify detector elements that are likely to produce z-axis artifacts in reconstructed images. The model curve is a second order polynomial which is fit to the set of attenuation signals and which is indicative of the correct profile projection through the reference phantom. Differences between a detector attenuation signal and this model curve is an indication of z-axis error produced by the detector element. Faulty or marginal detector elements are identified when this error becomes excessive.

BRIEF DESCRIPTION OF THE DRAWINGS

FIGS. 4(a)–(c) are graphic representations of three different z-axis sensitivity profiles of detectors used in the system of FIG. 1(a);

FIG. 5(a) is an exemplary x-ray flux density profile;

FIG. 5(b) is the resulting signals after air calibration produced by the detectors of FIGS. 4(a)–(c);

FIG. 6(a) is a second exemplary x-ray flux density profile;

FIG. 6(b) is the resulting signals after air calibration produced by the detectors of FIGS. 4(a)–(c);

FIGS. 7(a)–(b) are partial pictorial views of the CT scanner of FIG. 1 showing a test phantom in place.

DESCRIPTION OF THE PREFERRED EMBODIMENT

Figures 1A, 1B:
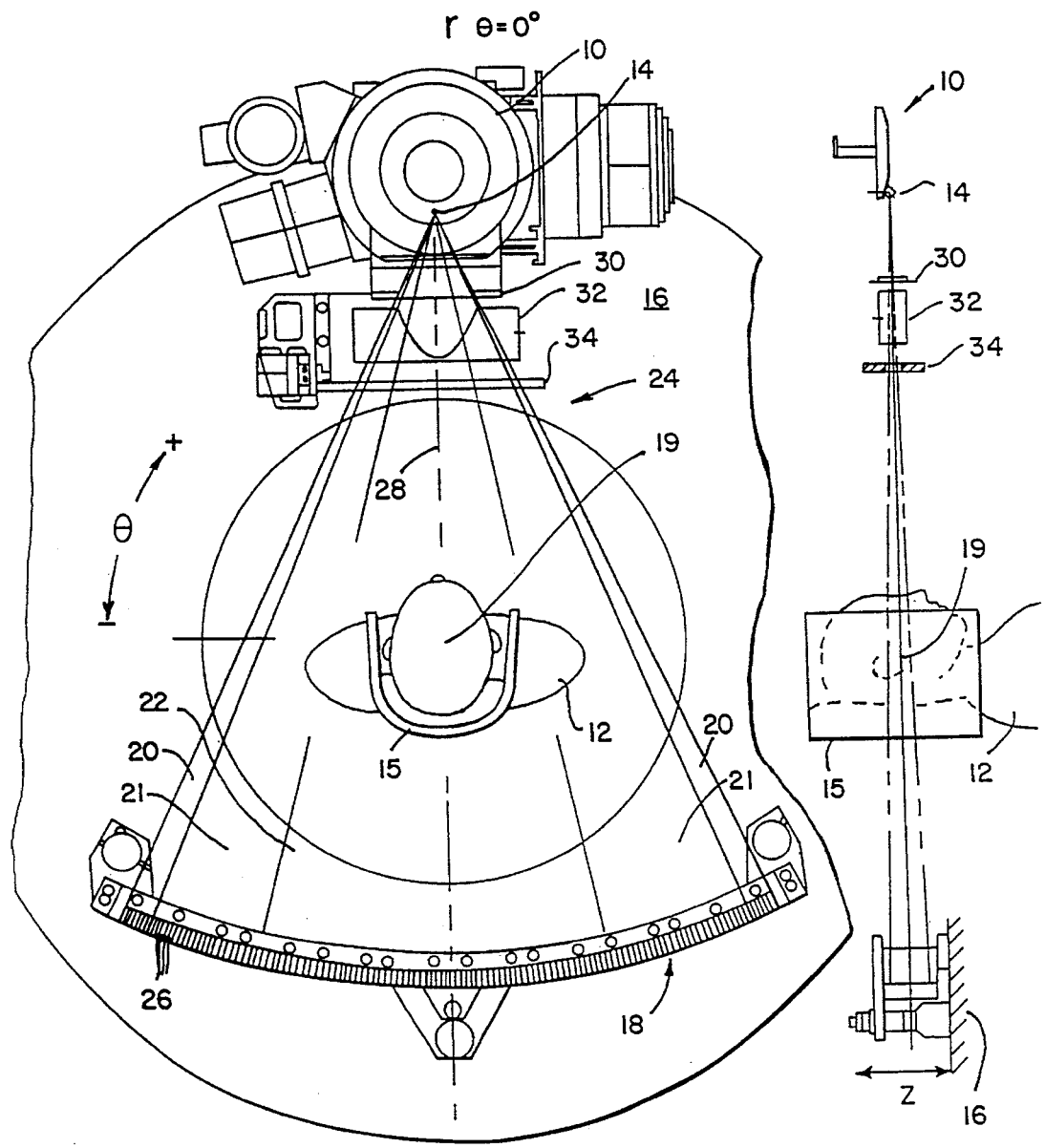
FIGS. 1(a)–(b) are front and side views, in elevation, of a CT gantry showing the relative positions of an x-ray source, detector array an fan beam about a patient's head.

Referring to FIG. 1, a CT gantry 16, representative of that used with a "third generation" CT scanner, holds an x-ray source 10 producing a fan beam of x-rays 24. The fan beam 24 is directed through a patient 12, positioned near a center 19 of the gantry 16, to be received by a detector array 18 also attached to the gantry 16. The patient's head is supported by a headholder 15.

The gantry 16 rotates within an x-y plane of a Cartesian coordinate system, termed the imaging plane, which is generally the same plane as that of the fan beam 24.

The detector array 18 is comprised of a number of detector elements or "channels" 26 positioned adjacent to each other within the imaging plane to subtend the fan beam 24. The channels 26 receive and detect radiation passing from the x-ray source 10, to produce a plurality of channel signals each associated with a particular channel 26. At a given orientation of gantry 16 about patient 12, signals for approximately 800 channels may be acquired, representing a detailed picture of the line integral of the attenuation of the fan beam 24 by the patient 12 at that angle. A gantry angle of zero is defined as that angle where a principle ray 28, centered in the fan beam 24, is directed vertically downward from the x-ray source 10.

The x-rays of the fan beam 24, immediately after leaving x-ray source 10 and prior to being received by the detector array 18, are filtered by a spectral filter 30 which filters out the lower energy x-rays from the fan beam 24. The fan beam 24 then passes through a bow tie filter 32 having a profile that produces an attenuation in the fan beam 24 complementing that which would be produced by a cylinder of water placed at the center 19 of the gantry 16. The purpose of the bow tie filter 32 is to reduce the range of intensity values received by the detector channels 26 for a typical patient 12 and hence to allow for an increase in sensitivity of the detector array 18 and its associated circuitry.

The bow tie filter 32 is followed by an aperture 34 which forms fan beam 24 and may be used to correct the position of the fan beam 24 with respect to the surface of the detector array 18 as described generally in U.S. Pat. No. 5,054,041 issued to the same assignee as that of the present application and incorporated herein by reference.

For a given patient 12, the channels 26 may be roughly divided into three groups: reference, over-range, and in-range. Reference channels 20 of the detector array 18 are those intended not to be occluded by the patient 12 or headholder 15 and may serve the function of calibrating the projection data for variations in the x-ray flux from x-ray source 10, and serve further to permit automatic alignment of the fan beam 24 on the detector array 18. Over-range channels 21 of the detector array 18 are those channels within a given projection which, although possibly occluded by the imaged object 12, generally receive x-rays having so little attenuation that the ADC, used to digitize the signals of these channels, is over-ranged. And finally, in-range channels 22 of the detector array 18, are those in a given projection which are sufficiently attenuated by the imaged object 12 so as not to over-range the ADC used to digitize the signals from these channels.

Figure 2:
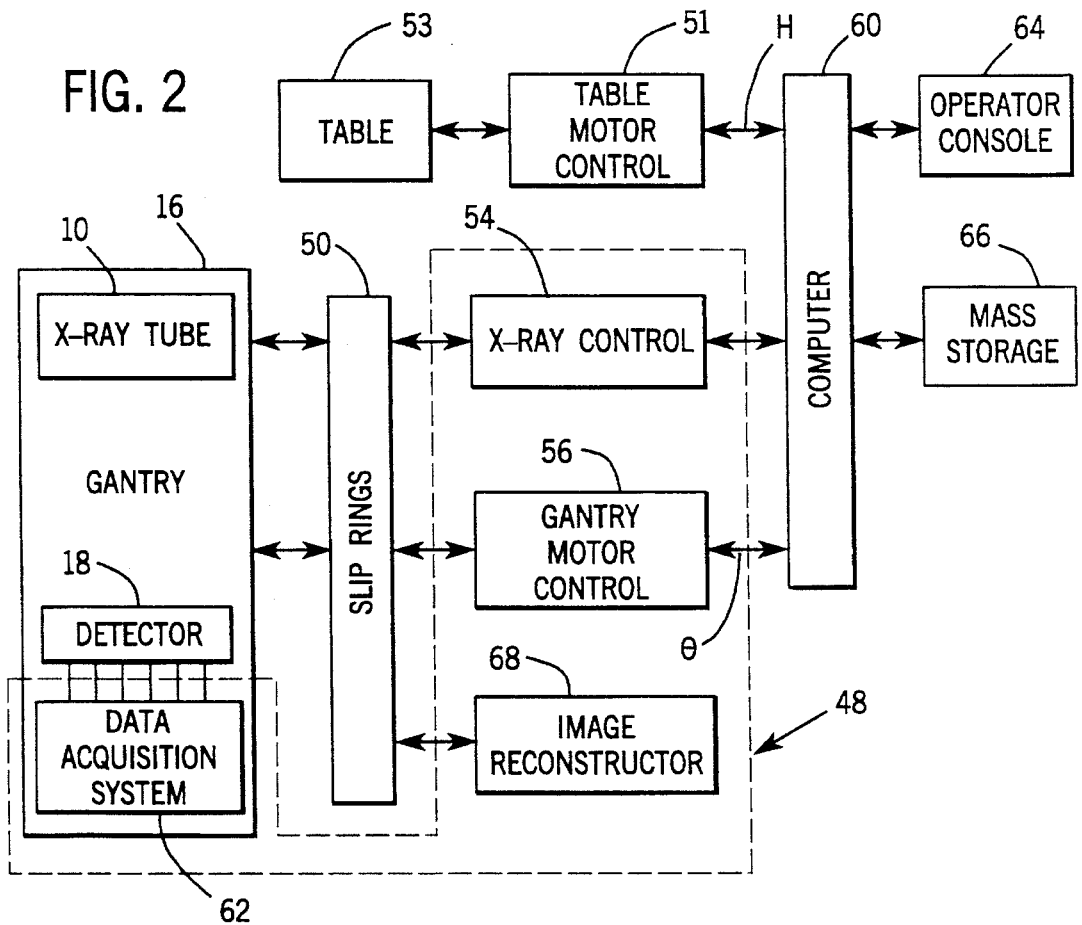
FIG. 2 is a block diagram of a CT control system associated with the gantry of FIG. 1 and used to practice the present invention.

Referring to FIG. 2, control circuitry for a CT imaging system suitable for use with the present invention includes a number of functional blocks 48. A data acquisition system 62 is connected to the detector array 18 and comprises a sampling means (not shown) for sampling the signals from each of the channels 26. An analog to digital converter ("ADC") (not shown) converts the sampled analog signals from each sampled channel 26 to a digital value for processing by later circuitry.

A radio translucent tube 53 supports the patient 12 and the headholder 15, the latter which is typically fixed to the table 53. The table 53 may be moved through the image plane to align the slice of interest of the patient with the image plane, and may be raised or lowered to center the patient 12 within the opening of the gantry 16. The movement of the table is accomplished by motors (not shown) controlled by table motor control 51. The table motor control 51 also generates a value H indicating the height of table 53 with respect to the iso-center 19.

An x-ray control 54 provides power and timing signals to the x-ray source 10 with regard to the position of gantry 16 to acquire the projections. Gantry motor controller 56 controls the rotational speed and position of the gantry 16 and provides gantry angle information θ to the DAS 62 and the x-ray control 54 to permit accurate timing of the projections.

The image reconstructor 68 is a special purpose computer, such as an array processor, capable of very rapid parallel processing or "pipelining" as is necessary to produce images from the large amount of projection data. Array processors suitable for use as the image reconstructor 68 are commercially available from a variety of sources. The image reconstructor 68 receives the sampled and digitized signals from the channels 26 of the detector array 18 via the DAS 62 to perform high speed image reconstruction according to methods known in the art.

A computer 60 coordinates the operation of the DAS 62, the table motor control, the x-ray control 54, and the gantry motor control 56 and works in conjunction with image reconstructor 68 to reconstruct tomographic images from the set of projections acquired by the scanning process. The computer 60 receives commands and scanning parameters via operator console 64 which is generally a CRT display and keyboard which allows the operator to enter parameters for the scan and to display the reconstructed slice images and other information from the computer 60. A mass storage device 66 provides a means for storing operating programs for the CT imaging system, as well as image data for future reference by the operator.

Each of the above elements is connected to its associated elements on the gantry 16 via slip rings 50 to permit continuous rotation of the gantry 16.

The present invention is implemented under the direction of a program executed by the computer 60. As will be described in more detail below, this program directs the CT system to acquire test data from a phantom which is designed to accentuate z-axis artifacts. The phantom may be made of any of a number of materials, but in the preferred embodiment it is made of an acrylic plastic such s that sole under the trademark PLEXIGLASS. As shown in FIGS. 7a and 7b, this phantom 80 has a circular perimeter 81 which is bevelled at a 65° angle with respect to the x-ray path. The phantom 80 is positioned concentric with the system iso-center and a scan comprised of 984 views is acquired as the gantry is rotated about the phantom 80. Each view includes separate values for each of the 852 detector elements which are pre-processed to compensate for differences in channel gain, detector offsets, beam hardening, etc. and conveyed to the computer 60.

Other phantoms may be used to obtain the detector deterioration signatures. All that is required is some means for producing an x-ray beam that is not uniform along the z axis. For example, a sloped bar phantom aligned parallel to the detector may be employed to produce such a non-uniform beam, and the attenuation data may be acquired without rotating the gantry.

Because detector deterioration can manifest itself differently under various operating conditions the test is repeated a number of times. In the preferred embodiment four separate test scans are performed on the phantom 80 using the following parameters:

| Tube Voltage | Slice Thickness |
| --- | --- |
| 120 kV | 5 mm |
| 120 kV | 10 mm |
| 140 kV | 5 mm |
| 140 kV | 10 mm |

The number of tests and the parameters of each test will, of course, be system specific, but as a general rule, they should sample the range of tube voltages and slice thicknesses commonly used in clinical applications.

Figure 3:
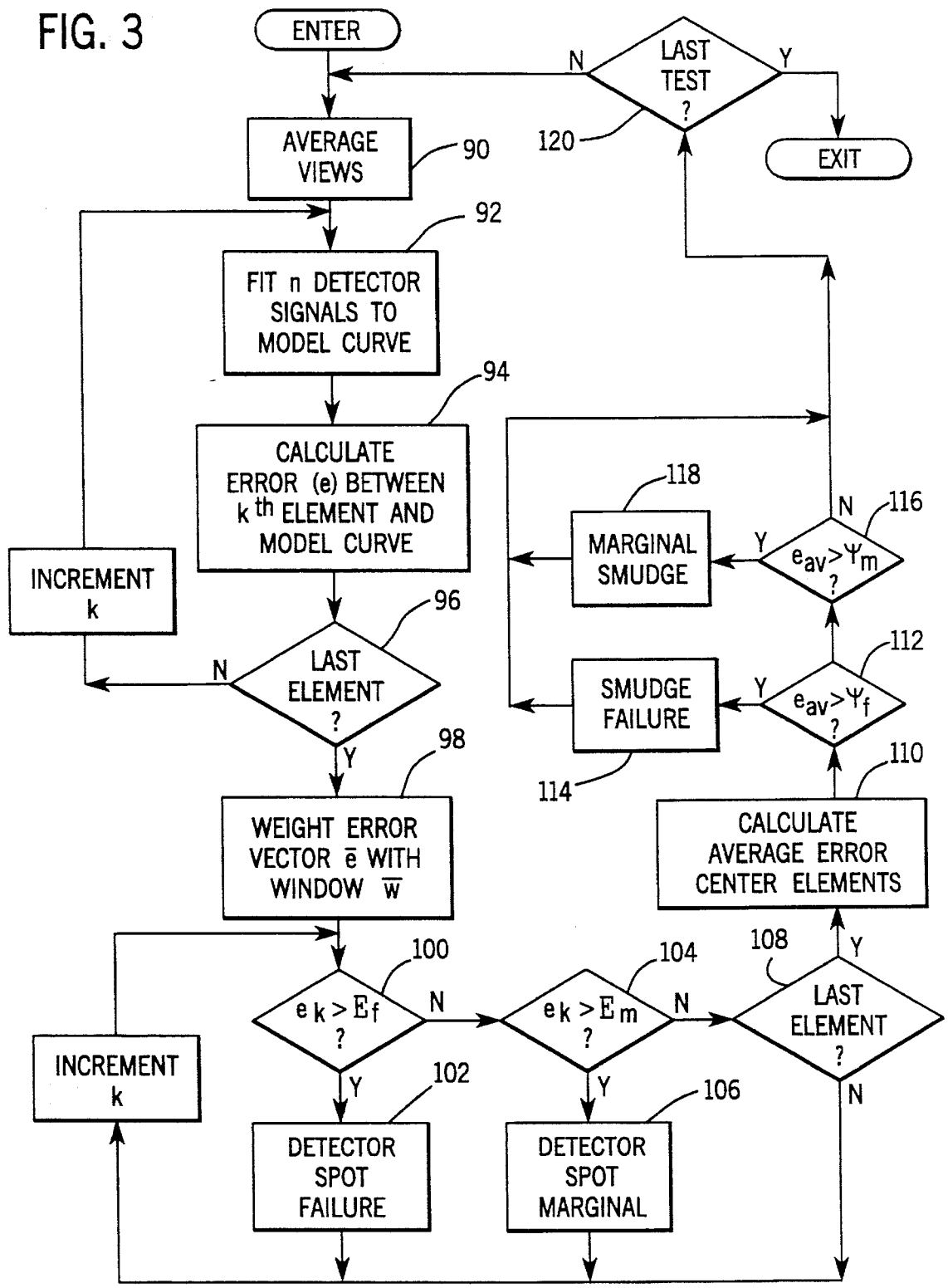
FIG. 3 is a block diagram showing the processing of the test data acquired by the CT system of FIG. 2 and used to evaluate detector performance according to the present invention.

Referring to FIG. 3, after the test data is acquired and pre-processed as described above, the computer 60 averages the separate readings for the 984 views as indicated at process block 90. This averaging is required to lower the statistical error (due to limited photons) at a level well below the z-axis errors that are being measured. A loop is then entered in which the error (e) of each detector reading is measured. In the preferred embodiment only the 65 detectors centered about the iso-center are examined, since it is the central detector channels that contribute most to z-axis artifacts.

As indicated at process blocks 92 and 94, the error (e) at the element k being examined is calculated in two steps. First, the n=41 detector readings centered about the element k are fit to a second order polynomial curve. Such a second order polynomial is a model of the ideal projection profile of the phantom 80. It should be apparent, however, that the phantom 80 can be shaped such that the resulting projection can be modeled exactly by a polynomial with a limited number of terms. Also, the polynomial fitting step is a low pass filtering process, and hence, other low pass filters may also be employed in place of the curve fitting process to arrive at a model curve that represents ideal performance. The absolute value of the difference between this model curve and the reading of the $k^{th}$ detector is then calculated as the error (e). This two step process is repeated for each of the 30 centered detector elements to produce a 30 element error vector $\vec{e}$. When all the errors have been calculated, as determined at decision block 96, the loop is exited.

The determination of n in the above process is not straight forward. If n is too small, the error detection process will not be sensitive to the wide band errors which result in large disc shaped artifacts at the center of the image. On the other hand, if n is chosen too large, an over-estimation of the errors in detectors may occur due to non-perfect beam hardening corrections or off-focal radiation corrections. The choice of n=41 is a compromise between these two conflicting requirements.

Figure 8:
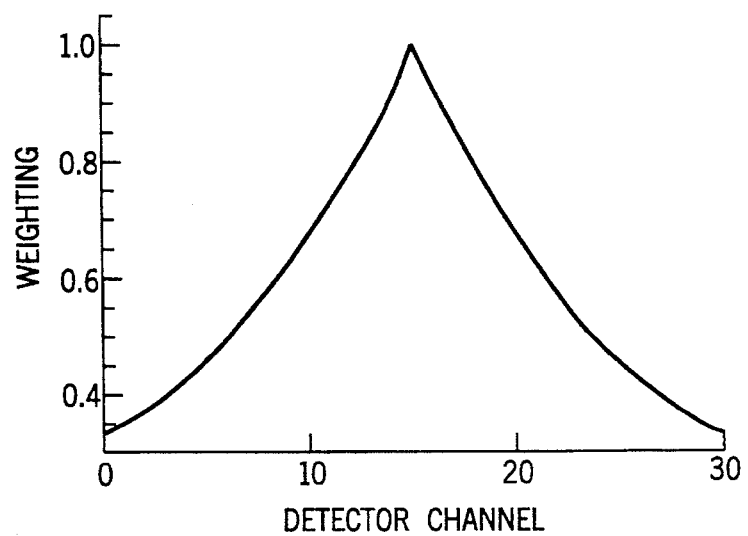
FIG. 8 is a graphic representation of a weighting factor W employed in the process of FIG. 3.

Because the tomographic reconstruction process places more importance on the readings of detectors located near the iso-center, errors in those readings will make a disproportionately greater contribution to image artifacts. As a result, the error vector $\vec{e}$ is multiplied by a weighting function $\vec{w}$ that increases sensitivity of the central detector measurements relative to the peripheral detector channels. The weighting function $\vec{w}$ is applied at process block 98 as an element by element multiplication of the two vectors $\vec{e}$ and $\vec{w}$. The preferred weighting function is illustrated by the graph in FIG. 8 and is defined by the following expression:

$$w_k = \frac{\alpha}{\alpha + x/\beta}$$

where $\alpha$ is a parameter set to 0.3, x is the distance (in terms of channels) from the iso-center channel, and $\beta$ is a control parameter set to 15.

Referring still to FIG. 3, after the errors are weighted a series of comparisons are made to test the integrity of each detector channel. A loop is entered in which each of the 30 detector error values in the windowed error vector $\vec{e}$ are compared with preset limits. As indicated at decision block 100, if the windowed error $e_k$ exceeds a first limit $\epsilon_f$, a detector spot failure is indicated at process block 102. Such a detector will produce a z-axis "spot artifact" in the image and should be replaced. As indicated at decision block 104, if the spot failure test is passed, the detector error $e_k$ is compared with a second limit $\epsilon_m$. If the error exceeds this second limit, the detector has marginal performance and this is indicated at process block 106. The detector errors are evaluated in this manner for spot producing detector degradation until all 30 elements have been examined as determined by decision block 108. An alternative procedure is to select the highest error (e) in the windowed error vector ($\vec{e}$) and compare it with the two limits $\epsilon_f$ and $\epsilon_m$. If neither limit is exceeded, then the evaluation is finished very quickly.

Even though individual detectors may not deteriorate enough to produce spot artifacts, the central most detectors may collectively deteriorate and produce a "smudge artifact" at the center of the image. This condition is tested by averaging the error values for the central detector elements at process block 110, and comparing this average error $e_{av}$ with preset limits. In the preferred embodiment the seven central detector errors are averaged to maintain sensitivity to smaller smudge artifacts while extending sensitivity to larger smudge artifacts. The average error $e_{av}$ is compared with a first limit $\psi_f$ at decision block 112, and if this limit is exceeded, a smudge failure is indicated at process block 114. If this limit is passed, a second limit $\psi_m$ is tested at decision block 116. If this second limit is exceeded, a marginal smudge is indicated at process block 118.

The limits $\epsilon_f$, $\epsilon_m$, $\psi_f$ and $\psi_m$ are determined empirically and will differ for different phantoms and different measurement technics. Thus, with the four different test conditions employed in the preferred embodiment, four different sets of these preset limits are required. As indicated in FIG. 3 at decision block 120, the procedure is repeated for all four test conditions with their respective sets of preset limits.

I claim:

1. A method for identifying deteriorated detector elements in a computed tomography system having an x-ray source for producing a fan beam of x-rays along a fan beam plane and with a thickness along an axis normal to the fan beam plane, and having a set of detector elements disposed in the fan beam of x-rays to produce a corresponding set of attenuation signals that indicate the x-ray flux density profile of the fan beam, the steps comprising:

a) acquiring a set of attenuation signals from the detector elements with a reference phantom disposed in the fan beam of x-rays that attenuates the x-rays such that the flux density of the x-rays striking the detector elements has a substantial gradient along the thickness direction;

b) calculating an error (e) for each of a plurality of detector elements centered about a system iso-center by comparing the value of the detector element attenuation signal with a model curve which represents an ideal x-ray flux density profile of the reference phantom; and c) comparing each detector element error (e) with a preset limit and indicating a faulty detector element when the error (e) exceeds the preset limit.

2. The method as recited in claim 1 in which step a) is repeated a plurality of times with the fan beam projected at different angles in the fan beam plane, and step b) is performed using the average of the plurality of sets of attenuation signals.

3. The method as recited in claim 1 in which the model curve is produced by fitting a second order polynomial to the set of attenuation signals, and the error (e) is calculated as the difference between the detector element attenuation signal and the model curve.

4. The method as recited in claim 1 in which the errors (e) calculated for the plurality of detector elements are multiplied by a window function (w) which weights the errors (e) associated with detector elements located near a system iso-center heavier than errors (e) associated with detector elements located further away from the system iso-center.

5. The method as recited in claim 1 which further includes:

d) averaging the errors (e) for a plurality of detector elements at a system iso-center; and e) comparing the average value calculated in step d) with a second preset limit and indicating a smudge failure when the average value exceeds the second preset limit.

* * * * *